(12) United States Patent
Neuber

(10) Patent No.: US 12,369,867 B2
(45) Date of Patent: Jul. 29, 2025

(54) TILTABLE COUCH BOARD

(71) Applicant: Siemens Healthineers AG, Forchheim (DE)

(72) Inventor: Wolfgang Neuber, Eschenbach I. D. Opf. (DE)

(73) Assignee: Siemens Healthineers AG, Forchheim (DE)

(*) Notice: Subject to any disclaimer, the term of this patent is extended or adjusted under 35 U.S.C. 154(b) by 403 days.

(21) Appl. No.: 17/896,196

(22) Filed: Aug. 26, 2022

(65) Prior Publication Data
US 2023/0063881 A1 Mar. 2, 2023

(30) Foreign Application Priority Data

Aug. 30, 2021 (DE) ..................... 20 2021 104 657.0

(51) Int. Cl.
*A61B 6/04* (2006.01)

(52) U.S. Cl.
CPC .......... *A61B 6/0487* (2020.08); *A61B 6/0407* (2013.01)

(58) Field of Classification Search
CPC ....... A61B 6/0487; A61B 6/04; A61B 6/0407; A61B 6/0428; A61B 6/0471; A61G 13/02; A61G 2203/42; A61G 13/04; A61G 13/08; A61G 7/0755; A47B 1/10; A47B 13/081

See application file for complete search history.

(56) References Cited

U.S. PATENT DOCUMENTS

| 2013/0111668 A1* | 5/2013 | Wiggers | A61N 5/1049 5/608 |
| 2016/0242981 A1* | 8/2016 | Debatty | A61N 5/1049 |

OTHER PUBLICATIONS

Civco Medical Solutions—Protura™ Robotic Patient Positioning System, (Stand: Jul. 8, 2020) https://web.archive.org/web/20200807073842/http://civcort.com/ro/robotics1/Protura-Robotic-Patient-Positioning-System.htm.

* cited by examiner

*Primary Examiner* — Justin C Mikowski
*Assistant Examiner* — Deborah Talitha Gedeon
(74) *Attorney, Agent, or Firm* — HARNESS, DICKEY & PIERCE, P.L.C.

(57) ABSTRACT

One or more example embodiments of the present invention relates to a tilt module for a patient couch, having a first support unit, a second support unit and a linear drive system, wherein one of the first support unit and the second support unit is configured to fix the tilt module to a stand of the patient couch or to receive a couch board, wherein the second support unit is connected via a joint to the first support unit at a tilt angle, wherein the linear drive system couples the first support unit and the second support unit such that the second support unit is tiltable relative to the first support unit along a circular-like travel path with simultaneous variation of the tilt angle due to a change in length of the linear drive system.

20 Claims, 3 Drawing Sheets

TILTABLE COUCH BOARD

CROSS-REFERENCE TO RELATED APPLICATION(S)

The present application claims priority under 35 U.S.C. § 119 to German Patent Application No. 202021104657.0, filed Aug. 30, 2021, the entire contents of which are incorporated herein by reference.

FIELD

One or more example embodiments of the present invention relates to a tilt module for a patient couch, to a tiltable couch board unit and to a patient couch.

BACKGROUND

A conventional couch board, which is used in medical imaging or medical radiation therapy, typically has at least one, customarily up to three translational degrees of freedom along the spatial axes x, y, z. Specific applications of a couch board in medical imaging or medical radiation therapy can also require at least one rotational degree of freedom. This rotational degree of freedom can make possible for example a tilting movement of the couch board. Typical tilting movements are "pitch" and "roll". The former describes a tilting movement about a longitudinal axis of the couch board, the latter describes a tilting movement about a transverse axis of the couch board. The longitudinal axis of the couch board is regularly referred to as a tip axis, the transverse axis of the couch board is regularly referred to as a cant axis.

A structural implementation of one or both tilting movements for the couch board, for example in the form of a tilt module, requires, in particular, additional installation space on a patient couch to which a tiltable couch board of this kind can be attached, and this in turn changes geometric properties of the patient couch itself. A tilt module of this kind should, for example, therefore preferably be as flat as possible in order to change the geometric properties of the patient couch as little as possible.

A tilt module, which makes possible at least one tilting movement and can be attached to a conventional patient couch, is known by the name of Protura belonging to the company Civco (see https://civcort.com/ro/robotics1/Protura-Robotic-Patient-Positioning-System.htm). The tilting movement of this tilt module can be made kinetically possible substantially by means of a hexapod arrangement.

SUMMARY

One or more example embodiments relates to a tilt module for a patient couch, a tiltable couch board unit and a patient couch, which are technically less complex and affect the geometric properties of the patient couch less.

According to one or more example embodiments, a tilt module for a patient couch includes a first support unit; a second support unit; and a linear drive system, wherein one of the first support unit and the second support unit is configured to fix the tilt module to a stand of the patient couch or to receive a couch board, the second support unit is connected via a joint to the first support unit at a tilt angle, and the linear drive system couples the first support unit and the second support unit such that the second support unit is tiltable relative to the first support unit along a circular-like travel path with simultaneous variation of the tilt angle due to a change in a length of the linear drive system.

According to one or more example embodiments, a direction of the change in the length of the linear drive system is perpendicular to a longitudinal axis of the second support unit.

According to one or more example embodiments, a direction of the change in the length of the linear drive system is parallel to a longitudinal axis of the second support unit.

According to one or more example embodiments, a direction of the change in the length of the linear drive system is perpendicular to the circular-like travel path.

According to one or more example embodiments, the linear drive system is configured in accordance with wedge sliding kinematics.

According to one or more example embodiments, the linear drive system includes a rolling apparatus with at least one roller at a first end of the linear drive system, the first support unit has a first guide rail in a region of the rolling apparatus, the first guide rail configured to guide the rolling apparatus, the second support unit has a second guide rail in the region of the rolling apparatus, the second guide rail configured to guide the rolling apparatus, wherein a position of the rolling apparatus along the first guide rail and along the second guide rail is adjustable based on the change in the length of the linear drive system, and the first guide rail and the second guide rail intersect.

According to one or more example embodiments, the rolling apparatus has a second roller.

According to one or more example embodiments, the first support unit and the second support unit are nested.

According to one or more example embodiments, the second support unit is a frame and surrounds the first support unit.

According to one or more example embodiments, the tilt module further includes a third support unit configured to receive the couch board or to fix the tilt module to a stand of the patient couch; and a second linear drive system, wherein the second linear drive system couples the third support unit to a coupled support unit such that a tilt angle between the third support unit and the coupled support unit is adjustable along a second circular-like travel path due to a second change in a length of the second linear drive system, the coupled support unit being the first support unit or the second support unit, wherein the second change in the length of the second linear drive system is perpendicular to the change in the length of the linear drive system.

According to one or more example embodiments, the direction of the second change in the length of the second linear drive system is perpendicular to the second circular-like travel path, and wherein the second linear drive system is designed for wedge sliding kinematics.

According to one or more example embodiments, the tilt module includes a third support unit configured to receive the couch board or to fix the tilt module to a stand of the patient couch; and an axial gear system, wherein the axial gear system couples the third support unit to the first support unit or the second support unit.

According to one or more example embodiments, the first support unit is arranged between the second support unit and the third support unit, wherein the third support unit is configured to fix the tilt module to a stand of the patient couch and wherein the second support unit is configured to receive the couch board.

According to one or more example embodiments, the second support unit is between the first support unit and the third support unit, wherein the first support unit is configured to fix the tilt module to a stand of the patient couch and wherein the third support unit is configured to receive the couch board.

According to one or more example embodiments, a tiltable couch board unit includes a tilt module according to at least one example embodiment; and a couch board attached to the tilt module.

According to one or more example embodiments, a patient couch includes a tilt module according to at least one example embodiment, wherein the tilt module is attached to the stand.

BRIEF DESCRIPTION OF THE DRAWINGS

At least some example embodiments of the present invention will be described and explained in more detail hereinafter with the aid of the exemplary embodiments illustrated in the figures. In principle, in the following description of the figures, structures and units that remain substantially identical will be labeled with the same reference characters as in the case of the first occurrence of the respective structure or unit.

In the drawings.

DETAILED DESCRIPTION

Figure 1:
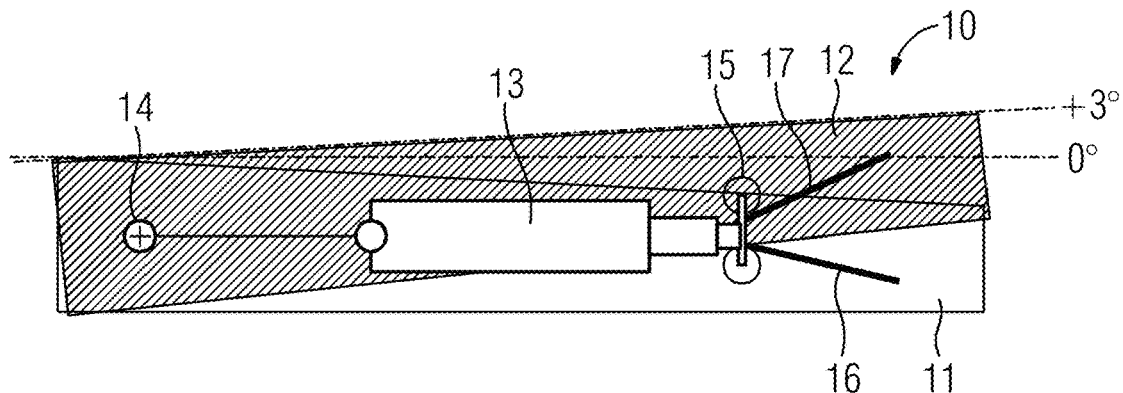
FIG. 1 shows an inventive tilt module in a first operating state according to an example embodiment.

An inventive tilt module for a patient couch has
a first support unit,
a second support unit and
a linear drive system,
wherein one of the two support units is designed for fixing the tilt module to a stand of the patient couch or for receiving a couch board,
wherein the second support unit is connected via a joint to the first support unit at a tilt angle,
wherein the linear drive system couples the first support unit and the second support unit in such a way that due to a change in length of the linear drive system the second support unit can be tilted relative to the first support unit along a circular path-like travel path with simultaneous variation of the tilt angle.

One advantage of the tilt module is that the coupling of the first support unit to the second support unit by the linear drive system represents simple kinematics in particular compared to a hexapod arrangement. This simple kinematics preferably builds on standard components, for example known from machine construction. Recourse to standard components typically comes with a price advantage, therefore. Alternatively or in addition, standard components are typically already tried and tested and thus advantageous for example in the case of handling and/or maintenance.

The tilt module for a patient couch is adapted in particular for application in medical imaging and/or in medical radiotherapy. The tilt module is configured in particular that a patient can be positioned on a couch board connected to the tilt module. The patient can have, for example, a weight of up to 300 kg or 400 kg.

The first support unit can be designed for fixing the tilt module to the stand of the patient couch. Alternatively, the second support unit can be designed for fixing the tilt module to the stand of the patient couch. The first support unit can be designed for receiving the couch board. Alternatively, the second support unit can be designed for receiving the couch board.

In principle it is conceivable that the first support unit is designed for fixing the tilt module to the stand of the patient couch and for receiving the couch board. Depending on the design of the second support unit, for example the tilt module can then simply be turned. Typically the first support unit can be designed for fixing the tilt module to the stand of the patient couch and the second support unit for receiving the couch board, or vice versa.

In general, the first support unit and the second support unit are designed to be arranged between the stand of the patient couch and the couch board and to couple them mechanically. In principle, for example, a third support unit or a platform or fixing means or comparable units can also be used for this coupling.

The first support unit and/or the second support unit is/are typically adapted in such a way that a further unit can be fixed to it and/or under it in a permanent, preferably detachable manner. The first support unit, the second support unit and the linear drive system form, in particular, a scaffold of the tilt module, which preferably structurally stabilizes and supports the tilt module.

If the first support unit and/or the second support unit is designed for receiving the couch board, the receiving support unit has, for example, a fixing means and/or a receiving apparatus, which interacts with the couch board in such a way that the couch board together with the tilt module can be used, in particular with a tilting movement, for example for medical imaging and/or the medical radiotherapy, without the couch board detaching from the tilt module.

If the first support unit and/or the second support unit is/are designed for fixing the tilt module to a stand of the patient couch, the support unit to be fixed has for example a fixing means and/or a fixing apparatus, which interacts with the stand of the patient couch in such a way that the patient couch together with the tilt module can be used, in particular with a tilting movement, for example for medical imaging and/or medical radiotherapy, without the tilt module detaching from the stand.

That the second support unit can be tilted relative to the first support unit, comprises in particular that the first support unit can be tilted relative to the first support unit. The tilt can substantially be defined as a function of a choice of reference system, it being possible for the first support unit or the second support unit to serve as a 0° axis.

The first support unit and/or the second support unit is/are typically designed to be elongate and/or rectangular. With an elongate design, a longitudinal axis is typically longer than a transverse axis. In principle it is conceivable that the first support unit and/or the second support unit is/are square. With a square design, a longitudinal axis has the same length as a transverse axis, and vice versa.

The joint can in particular make possible the tilt in the form of a rotation of the second support unit relative to the first support unit about an axis of rotation. In this case the joint can in particular be a swivel joint. Depending on the design of the joint, the joint can to a certain extent also make a translation possible. In principle it is conceivable that the joint makes possible a tilt angle of up to and including ±180°. The tilt angle is regularly less than ±90°, advantageously ±45°, preferably ±25°, in particular ±10°. Furthermore, it is conceivable that the amount of the enabled tilt angle greater than zero differs from the amount of the enabled tilt angle less than zero. In principle, forces acting on the linear drive system, in particular if the linear drive system is designed for wedge sliding kinematics, are all the greater, the greater the tilt angle is.

Direction and/or length of the circular path-like travel path typically depend on the type of joint. The circular path-like travel path has in particular a length, which matches a tilt angle with an amount greater than 0'. The tilting movement of the couch board takes place in particular relative to, preferably along, the circular path-like travel path. The position of the circular path-like travel path relative to the joint, in other words the radius, can be arbitrarily defined along the first support unit or second support unit. This position can coincide for example with a fixing point.

The linear drive system can be fixed to the first support unit and to the second support unit at one fixing point each. In this case the linear drive system is adapted in particular to adjust the distance between the two fixing points due to the change in length. The fixing point of the first support unit and/or the fixing point of the second support unit can have, for example, a further joint and/or a bearing. The change in length of the linear drive system typically correlates with a change in the distance between the two fixing points. It is conceivable that, according to amount, the change in length of the linear drive system matches the change in the distance between the two fixing points.

The change in length refers in particular to a length of the linear drive system, with the length typically being defined from one end to another end of the linear drive system. The change in length describes in particular a change in the distance of the two ends of the linear drive system. The linear drive system can be fixed for example to the two ends in each case by a fixing point of the first support unit or of the second support unit respectively. The change in length can in particular be increasing if the distance of the two ends of the linear drive system becomes greater, and be reducing if the distance of the two ends of the linear drive system becomes smaller. The change in length is in particular more than 1 mm, preferably 10 mm, and/or less than 500 mm, preferably 100 mm.

The linear drive system enables in particular a linear change in length. The linear drive system can be designed in particular as an electromechanical drive unit or as a hydraulic cylinder unit. Suitable electromechanical drive units are in particular ball screws, trapezoidal spindles, planetary roller screw drives, rack-and-pinion drives or comparable drives. Alternatively or in addition, the linear drive system can have a traction mechanism such as a cable or a chain, which circumferentially arranged can act in both directions. Owing to the coupling to the first support unit and the second support unit, the change in length can in particular result in the linear drive system being tilted, typically about half of the tilt angle.

The tiltability of the second support unit relative to the first support unit due to the change in length of the linear drive system comprises an enlargement and reduction of the tilt angle. In other words, the tilt angle can become larger in particular due to an increasing change in length and the tilt angle can become smaller due to a reducing change in length. Tiltable means, in particular, that the second support unit can be moved relative to the first support unit along the circular path-like travel path with simultaneous variation of the tilt angle. In other words, the tilt angle between the second support unit relative to the first support unit can be adjusted due to the change in length of the linear drive system.

With simultaneous variation of the tilt angle means that the tilting of the second support unit relative to the first support unit may be mapped and/or read off directly in the variation of the tilt angle. The variation of the tilt angle comprises in particular becoming larger and smaller.

The relative indication, used hereinafter, of the geometric orientation of the different units to each other by the term "perpendicular" means, in particular, substantially perpendicular. Use of the term perpendicular does not limit the orientation to an angle of exactly 90° therefore but, on the contrary, in particular depending on the exemplary embodiment and context of the indication, can mean merely that the mutual orientation is not parallel, but, for example, oblique. Advantageously the term perpendicular in this application comprises an angle range from 45° to 135°, preferably from 67.5° to 112.5°, in particular from 80° to 100°. The term perpendicular does not require axes oriented perpendicular to each other to necessarily intersect at a shared point either. In other words, the situation can occur where axes intersect only when they are (notionally) shifted within the planes specified by their respective units. Furthermore, the wording of the perpendicular orientation of different axes includes planes, in which the axes are located, intersecting at this perpendicular angle.

One embodiment provides that the direction of the change in length of the linear drive system is perpendicular to a longitudinal axis of the second support unit. This embodiment therefore describes in particular the roll-tilting movement about a transverse axis of the second support unit. Particularly advantageously this embodiment therefore makes it possible that, relative to a patient positioned on an attached couch board, the patient can be laterally tilted by way of the tilt module.

An alternative embodiment to the previous embodiment provides that the direction of the change in length of the linear drive system is parallel to a longitudinal axis of the second support unit. This embodiment thus describes in particular the pitch-tilting movement about a longitudinal axis of the second support unit. Particularly advantageously this embodiment thus makes it possible that, relative to a patient positioned on an attached couch board, tilting can take place over the length of the patient by way of the tilt module.

One embodiment provides that the linear drive system is arranged in such a way that the direction of the change in length of the linear drive system is perpendicular to the circular path-like travel path. With a tilt angle of 0° the change in length takes place, at least initially, typically within the plane spanned by the first support unit or the second support unit. The linear drive system is, at least initially, oriented parallel in particular relative to the first support unit or to the second support unit. Advantageously, positioning accuracy is increased in that, owing to the parallel orientation of the linear drive system, a greater change in length is necessary compared to a design when the linear drive system is oriented perpendicularly. In other words, a great change in length typically generates only a relatively small change in tilt angle.

One embodiment provides that the linear drive system is designed in accordance with wedge sliding kinematics. This embodiment is advantageous in particular because, as a result, a mechanical reduction is achieved, which makes a comparatively small drive force possible. Alternatively or in addition, preferably a higher patient load and/or a greater load moment is/are possible as a function of the distance of the positioned patient from the joint. A further advantage of this embodiment is an increased overload capacity, wherein simultaneously, due to the kinematic reduction ratio, typically only a fraction of the external load, in particular the patient load, acts on the linear drive system.

One embodiment provides that at a first end the linear drive system has a rolling apparatus with at least one roller, wherein in the region of the rolling apparatus the first support unit has a first guide rail for guiding the rolling apparatus, wherein in the region of the rolling apparatus the second support unit has a second guide rail for guiding the rolling apparatus, wherein the position of the rolling apparatus along the first guide rail and along the second guide rail can be adjusted by the change in length of the linear drive system and wherein the first guide rail and the second guide rail intersect. Depending on the design of the rolling apparatus and/or the first guide rail and/or the second guide rail, a force absorption is possible in the pulling or pushing direction between the rolling apparatus and the first guide rail or the second guide rail. In this case a torque can be absorbed in one of the two directions. The first guide rail and/or the second guide rail can have an encompassing design, so a force absorption is possible in the pulling or pushing direction between the rolling apparatus and the first guide rail or the second guide rail. In other words, in this case a torque can be absorbed in both directions. The adjustability of the position of the rolling apparatus along the first guide rail and along the second guide rail typically takes place owing to a rolling movement and/or sliding movement of the rolling apparatus relative to the two guide rails. The rolling apparatus and the first guide rail and/or the second guide rail can be designed in the manner of a recirculating ball bearing guide system, ball bushing guide system, recirculating roller guide system and/or linear guide system with at least one slide bearing. That the first guide rail and the second guide rail intersect means, in particular, that the first guide rail and the second guide rail are conically arranged. If the rolling apparatus has only one roller, the rolling apparatus is typically arranged in such a way that the roller, in the case of an increasing change in length, presses the crossed guide rails apart, in particular in a wedge-like manner.

One embodiment provides that the rolling apparatus has a second roller. In this case the two rollers of the rolling apparatus are typically arranged in such a way that the two rollers are arranged outside of the first guide rail and the second guide rail and with a change in length the first guide rail and the second guide rail are situated between the two rollers.

One embodiment provides that the first support unit and the second support unit are arranged nested inside each other. This embodiment makes possible a space-saving arrangement of the first support unit and the second support unit and thus a more compact construction of the tilt module.

One embodiment provides that the second support unit is designed as a frame and surrounds the first support unit. This embodiment is advantageous in particular if the inner dimension of the second support unit is matched to an outer dimension of the first support unit in such a way that the distance between the first support unit and the second support unit is minimal.

One embodiment provides that the tilt module has a third support unit, in particular for receiving the couch board or for fixing the tilt module to a stand of the patient couch, and a second linear drive system, wherein the second linear drive system couples the third support unit to the first support unit or the second support unit in such a way that due to a second change in length of the second linear drive system a tilt angle between the third support unit and the support unit coupled to it can be adjusted along a second circular path-like travel path, wherein the second change in length of the second linear drive system runs perpendicular to the change in length of the linear drive system. The third support unit described in this embodiment and the second linear drive system can substantially be constructed like the above-described first support unit or second support unit and the linear drive system. This embodiment primarily describes that the tilt module can make possible two tilting movements in two different directions, in particular the roll-tilting movement and the pitch-tilting movement. In particular a second joint can be provided for this, which connects the second support unit to the third support unit or the first support unit to the third support unit at a second tilt angle. Depending on the design of the tilt module, in particular one of the three support units is designed for fixing the tilt module to the stand of the patient couch and another of the three support units is designed for receiving the couch board. Typically the last support unit arranged between these support units can likewise be designed for fixing the tilt module to the stand of the patient couch and for receiving the couch board in order to increase the reusability of the support units in the sense of a construction kit.

An alternative embodiment to the previous embodiment provides that the tilt module has a third support unit in particular for receiving the couch board or for fixing the tilt module to a stand of the patient couch and an axial gear system, wherein the axial gear system couples the third support unit to the first support unit or the second support unit. The axial gear system preferably simultaneously acts as a shaft and as a drive unit. The axial gear system can have an axial gear, in particular a cycloidal gear, a planetary gear, a HarmonicDrive gear, a Spirodrive gear and/or a worm gear. The design with the cycloidal gear is particularly advantageous owing to its rigidity, precision, compactness and/or torque. The axial gear advantageously forms the roll shaft. The drive of the axial gear takes place in particular by a drive motor flanged to the axial gear. The axial gear can have a self-locking or non-self-locking design. As a function thereof the drive motor has for example a brake and/or a self-locking transmission. Position detection, that is to say angle measurement, for the axial gear system can take place for example by a rotary encoder of the axial gear or by a linear measuring system. The linear measuring system measures, for example, a radian measure on a radial contour in the mechanical structure about the shaft. Advantageously, position detection or angle measurement can thus take place comparatively accurately via a corresponding trigonometric function. This embodiment is advantageous in particular because the axial gear can fulfil the function of the gear and also the shaft, that is to say a support and/or an absorption of the occurring forces, so overall fewer components are necessary. Furthermore, axial gears regularly provide high rigidity and/or precision and/or compactness and/or torque. The drive of the axle directly by the axial gear preferably allows a simple positionability and/or controllability. A further advantage of this embodiment relates to the compact construction and/or the comparatively maintenance-free operation.

One embodiment provides that the first support unit is arranged between the second support unit and the third support unit, wherein the third support unit is designed for fixing the tilt module to a stand of the patient couch and wherein the second support unit is designed for receiving the couch board. An alternative embodiment to the previous embodiment provides that the second support unit is arranged between the first support unit and the third support unit, wherein the first support unit is designed for fixing the tilt module to a stand of the patient couch and wherein the third support unit is designed for receiving the couch board.

One embodiment provides that the second linear drive system is arranged in such a way that the direction of the second change in length of the second linear drive system is perpendicular to the second circular path-like travel path, and that the second linear drive system is designed for wedge sliding kinematics. This embodiment is advantageous in particular because both tilting movements profit from the above-described advantages of wedge sliding kinematics.

An inventive tiltable couch board unit has
  a tilt module and
  a couch board attached to the tilt module for positioning a patient. The couch board unit has the inventive tilt module, so the couch board unit shares the above-described advantages. The couch board can in particular be designed to have such a length, and thus protrude beyond the support unit, that the center of gravity of the couch board, in particular following positioning of a patient on the couch board, acts outside of the tilt module. Alternatively, the couch board can substantially be so long that it covers the tilt module and the center of gravity of the couch board acts inside the tilt module.

An inventive patient couch has
  a tilt module or
  a tiltable couch board unit and
  a stand, wherein the tilt module is attached to the stand. The patient couch has the inventive tilt module, so the patient couch shares the above-described advantages. The stand can in particular be movable and/or motorized. The stand is typically adjustable in height in the vertical direction.

FIG. 1 shows a cross-section through an inventive tilt module 10 in a first operating state.

The tilt module 10 for a patient couch 30 has a first support unit 11, a second support unit 12 and a linear drive system 13. One of the two support units 11, 12 is designed for fixing the tilt module 10 to a stand 31 of the patient couch 30 or for receiving a couch board 21. The second support unit 12 is connected by a joint 14 to the first support unit 11 at a tilt angle. The tilt angle in this first operating state is +3°.

The linear drive system 13 couples the first support unit 11 and the second support unit 12 in such a way that due to a change in length of the linear drive system 13, the second support unit 12 can be tilted relative to the first support unit 11 along a circular path-like travel path with simultaneous variation of the tilt angle. The linear drive system 13 is arranged in such a way that the direction of the change in length of the linear drive system 13 is perpendicular to the circular path-like travel path. The linear drive system 13 is designed in accordance with wedge sliding kinematics. At a first end linear the drive system 13 has a rolling apparatus 15 with a roller and a second roller. In the region of the rolling apparatus 15 the first support unit 11 has a first guide rail 16 for guiding the rolling apparatus 15. In the region of the rolling apparatus 15 the second support unit 12 has a second guide rail 17 for guiding the rolling apparatus 15. The position of the rolling apparatus 15 can be adjusted along the first guide rail 16 and along the second guide rail 17 due to the change in length of the linear drive system 13. The first guide rail 16 and the second guide rail 17 intersect.

Figure 2:
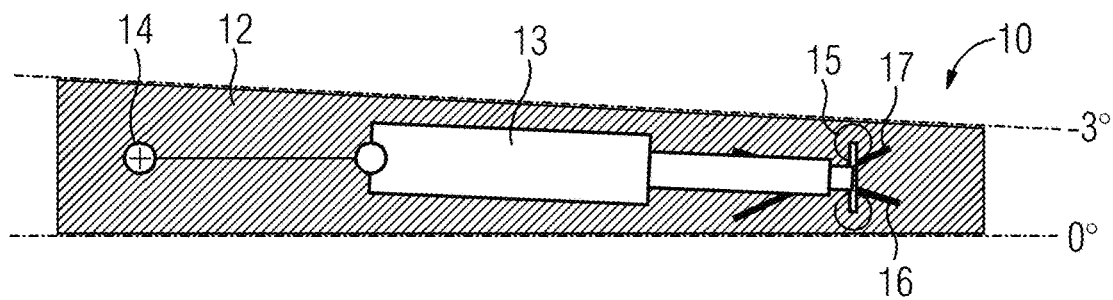
FIG. 2 shows the inventive tilt module in a second operating state according to an example embodiment.

FIG. 2 shows the inventive tilt module 10 in a second operating state in a side view.

The second operating state differs from the first operating state in the length of the linear drive system 13 owing to an increasing change in length that has taken place. In other words, in the second operating state the length of the linear drive system 13 is greater than in the first operating state. The tilt angle in this second operating state is −3°. For reasons of clarity FIG. 2 does not show the first support unit 11.

Figure 3:
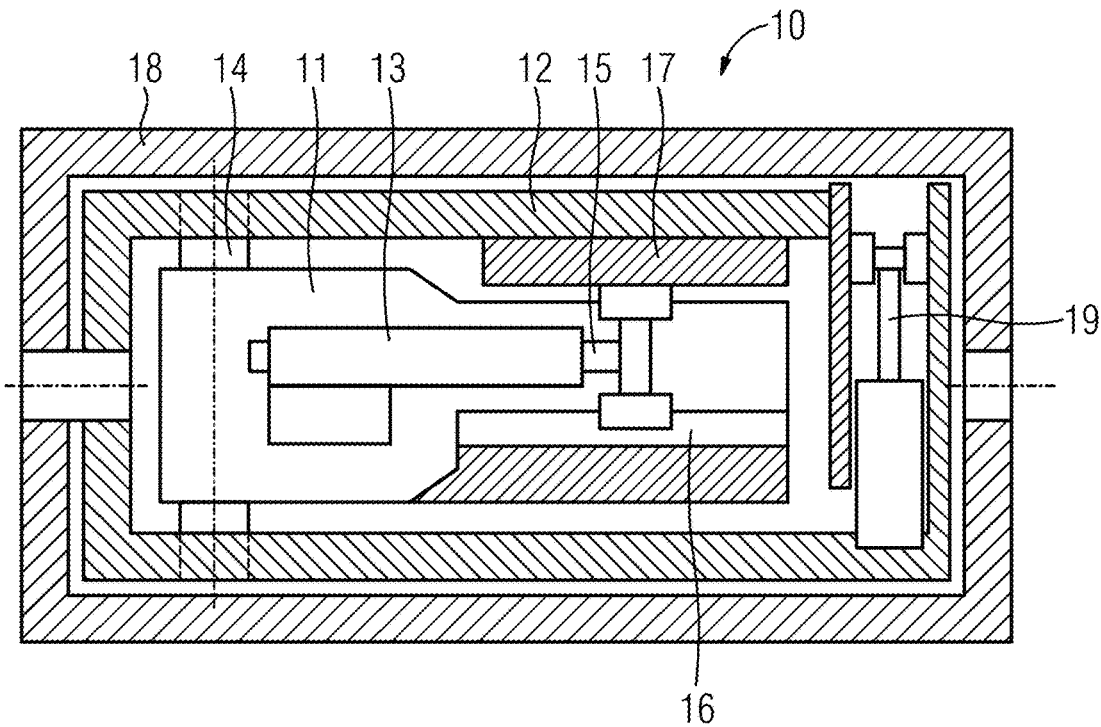
FIG. 3 shows the tilt module in a further exemplary embodiment.

FIG. 3 shows the tilt module 10 in a further exemplary embodiment from a bird's eye view.

The tilt module 10 also has a third support unit 18, which can be designed in particular for receiving the couch board 21 (not shown in FIG. 3) or for fixing the tilt module 10 to a stand 31 (not shown in FIG. 3) of the patient couch 30. Furthermore, the tilt module 10 has a second linear drive system 19. The second linear drive system 19 couples the third support unit 18 to the second support unit 12 in such a way that due to a second change in length of the second linear drive system 19, a tilt angle between the third support unit 18 and the second support unit 12 coupled to it can be adjusted along a second circular path-like travel path. In this exemplary embodiment, the second support unit 12 is arranged between the first support unit 11 and the third support unit 18, with the first support unit 11 being designed for fixing the tilt module 10 to a stand 31 (not shown in FIG. 3) of the patient couch 30 and with the third support unit 18 being designed for receiving the couch board 21 (not shown in FIG. 3). The second change in length of the second linear drive system 19 runs perpendicular to the change in length of the linear drive system 13.

The direction of the change in length of the linear drive system 13 is parallel to a longitudinal axis of the second support unit 12. The direction of the change in length of the second linear drive system 19 is perpendicular to the longitudinal axis of the second support unit 12. The second linear drive system 19 is arranged in such a way that the direction of the second change in length of the second linear drive system 19 is perpendicular to the second circular path-like travel path. The second linear drive system 19 is designed for wedge sliding kinematics and accordingly has a further rolling apparatus and additional guide rails, which are arranged on the second support unit 12 and the third support unit 18. The wedge sliding kinematics of the second linear drive system 19 differ substantially only in the orientation of the wedge sliding kinematics of the linear drive system 13.

The second support unit 12 is designed as a frame and surrounds the first support unit 11. Furthermore, the third support unit 18 is designed as a frame and surrounds the second support unit 12. The first support unit 11, the second support unit 12 and the third support unit 18 are thus arranged nested inside each other.

In an alternative embodiment (not shown), the first support unit 11 can be arranged between the second support unit 12 and the third support unit 18, with the third support unit 18 being designed for fixing the tilt module 10 to a stand 31 of the patient couch 30 and with the second support unit 12 being designed for receiving the couch board 21. In such an embodiment, the second linear drive system 19 couples the third support unit 18 to the first support unit 11 instead of to the second support unit 12, so due to the second change in length of the second linear drive system 19, a tilt angle can be adjusted between the third support unit 18 and the first support unit 11 coupled to it along the second circular path-like travel path.

Figure 4:
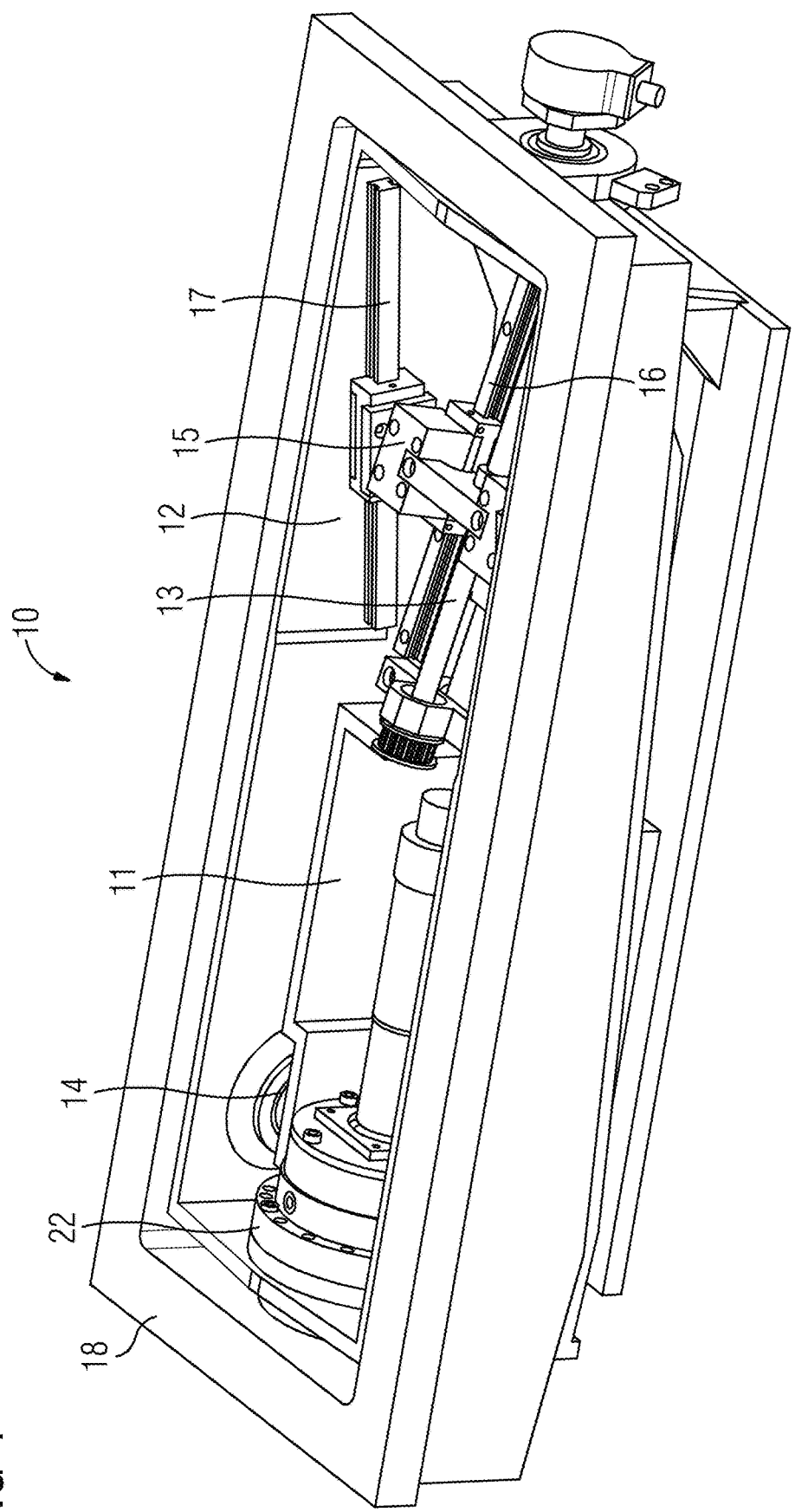
FIG. 4 shows the tilt module in an alternative exemplary embodiment.

FIG. 4 shows the tilt module 10 in an alternative exemplary embodiment to the exemplary embodiment shown in FIG. 3 from a perspective view.

The tilt module 10 also has a third support unit 18, which can be designed in particular for receiving the couch board 21 (not shown in FIG. 4) or for fixing the tilt module 10 to a stand 31 (not shown in FIG. 4) of the patient couch 30. Furthermore, the tilt module 10 has an axial gear system 22. The axial gear system 22 couples the third support unit 18 to the second support unit 12.

Figure 5:
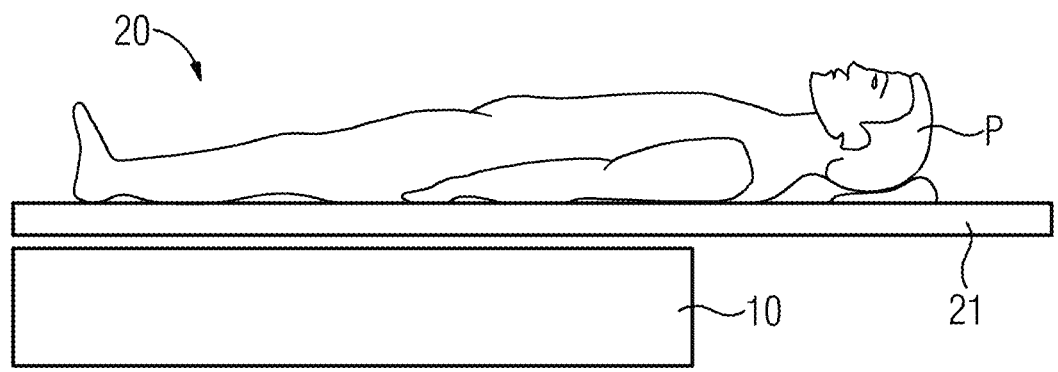
FIG. 5 shows an inventive tiltable couch board unit according to an example embodiment.

FIG. 5 shows an inventive tiltable couch board unit 20 in a side view.

The tiltable couch board unit 20 has a tilt module 10 and a couch board 21 attached to the tilt module 10 for positioning a patient P. The couch board 21 is attached to the tilt module 10 for example by a fixing means. The couch board 21 is preferably detachably fixed to the tilt module 10. In this exemplary embodiment, the couch board 21 protrudes beyond the tilt module 10. Depending on the positioning of the patient P and/or according to the weight of the patient P, the center of gravity can be outside or inside of the tilt module 10. The couch board 21 and/or the tilt module 10 are adapted in particular for an application in medical imaging and/or medical radiotherapy. The couch board can be for example at least partially transparent for X-ray radiation in medical imaging or for radiation in medical radiotherapy.

Figure 6:
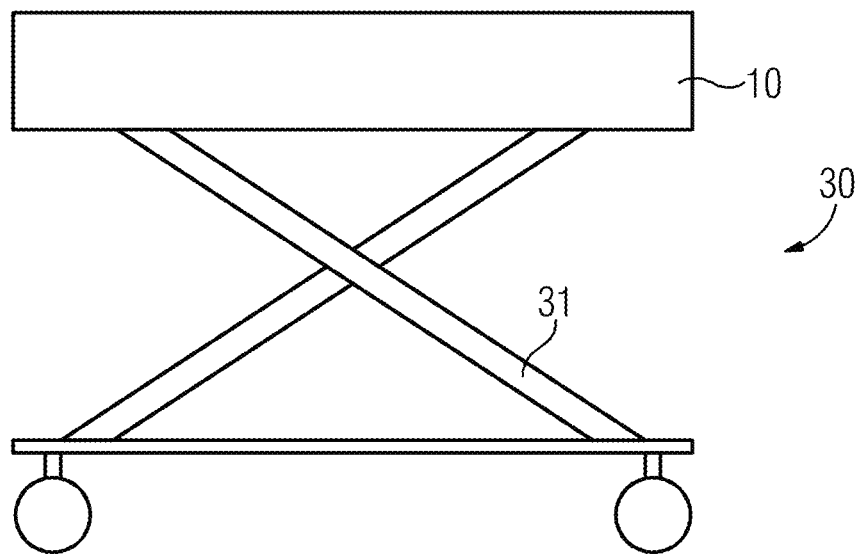
FIG. 6 shows an inventive patient couch according to an example embodiment.

FIG. 6 shows an inventive patient couch 30 in a side view.

The patient couch 30 has a tilt module 10 and a stand 31. The tilt module 10 is attached to the stand 31, for example by a fixing means. The stand 31 has lift kinematics. In addition, the patient couch 30 is designed to be movable by rollers attached to the stand. The couch board, which can also be attached to the tilt module 10, is not shown in FIG. 5.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling.

Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure is be thorough and complete, and fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments of the present invention. This invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art.

Although some example embodiments of the present invention have been illustrated and described in detail by the preferred exemplary embodiments, it is nevertheless not limited by the disclosed examples and a person skilled in the art can derive other variations herefrom without departing from the scope of the present invention.

The invention claimed is:

1. A tilt module for a patient couch, comprising:
   a first support unit;
   a second support unit;
   a third support unit;
   a first linear drive system; and
   a second linear drive system,
   wherein one of the first support unit, the second support unit, and the third support unit is configured to fix the tilt module to a stand of the patient couch or to receive a couch board,
   the second support unit is connected via a joint to the first support unit at a tilt angle,
   the first linear drive system couples the first support unit and the second support unit such that the second support unit is tiltable relative to the first support unit along a circular travel path with simultaneous variation of the tilt angle due to a change in a length of the first linear drive system, and
   the second linear drive system couples the third support unit to a coupled support unit such that a tilt angle between the third support unit and the coupled support unit is adjustable along a second circular travel path due to a second change in a length of the second linear drive system.

2. The tilt module of claim 1, wherein a direction of the change in the length of the first linear drive system is perpendicular to a longitudinal axis of the second support unit.

3. The tilt module of claim 2, wherein a direction of the change in the length of the first linear drive system is perpendicular to the circular travel path.

4. The tilt module of claim 1, wherein a direction of the change in the length of the first linear drive system is parallel to a longitudinal axis of the second support unit.

5. The tilt module of claim 4, wherein a direction of the change in the length of the first linear drive system is perpendicular to the circular travel path.

6. The tilt module of claim 1, wherein a direction of the change in the length of the first linear drive system is perpendicular to the circular travel path.

7. The tilt module of claim 6, wherein the first linear drive system is configured in accordance with wedge sliding kinematics.

8. The tilt module of claim 7, wherein
   the first linear drive system includes a rolling apparatus with at least one roller at a first end of the first linear drive system,
   the first support unit has a first guide rail in a region of the rolling apparatus, the first guide rail configured to guide the rolling apparatus,
   the second support unit has a second guide rail in the region of the rolling apparatus, the second guide rail configured to guide the rolling apparatus, wherein a position of the rolling apparatus along the first guide rail and along the second guide rail is adjustable based on the change in the length of the first linear drive system, and the first guide rail and the second guide rail intersect.

9. The tilt module of claim 8, wherein the rolling apparatus has a second roller.

10. The tilt module of claim 8, wherein the first support unit and the second support unit are nested.

11. The tilt module of claim 6, wherein the first support unit and the second support unit are nested.

12. The tilt module of claim 1, wherein the first support unit and the second support unit are nested.

13. The tilt module of claim 12, wherein the second support unit is a frame and surrounds the first support unit.

14. The tilt module of claim 1, wherein
   the coupled support unit is the first support unit or the second support unit, and
   the second change in the length of the second linear drive system is perpendicular to the change in the length of the first linear drive system.

15. The tilt module of claim 14, wherein a direction of the second change in the length of the second linear drive system is perpendicular to the second circular travel path, and wherein the second linear drive system is configured for wedge sliding kinematics.

16. The tilt module of claim 14, wherein the first support unit is arranged between the second support unit and the third support unit, wherein the third support unit is configured to fix the tilt module to a stand of the patient couch and wherein the second support unit is configured to receive a couch board.

17. The tilt module of claim 14, wherein the second support unit is between the first support unit and the third support unit, wherein the first support unit is configured to fix the tilt module to a stand of the patient couch and wherein the third support unit is configured to receive a couch board.

18. The tilt module of claim 1, wherein
   the third support unit is configured to receive a couch board or to fix the tilt module to a stand of the patient couch; and
   the coupled support unit is the first support unit or the second support unit.

19. A tiltable couch board unit, comprising:
   the tilt module of claim 1; and
   a couch board attached to the tilt module.

20. A patient couch, comprising:
the tilt module of claim 1, wherein the tilt module is attached to a stand.

\* \* \* \* \*